United States Patent
Loose et al.

(10) Patent No.: US 10,529,470 B2
(45) Date of Patent: Jan. 7, 2020

(54) CERAMIC CARRIER AND SENSOR ELEMENT, HEATING ELEMENT AND SENSOR MODULE, EACH WITH A CERAMIC CARRIER AND METHOD FOR MANUFACTURING A CERAMIC CARRIER

(71) Applicant: HERAEUS SENSOR TECHNOLOGY GMBH, Hanau (DE)

(72) Inventors: Thomas Loose, Linsengericht (DE); Stefan Dietmann, Alzenau (DE); Alfred Fleckenstein, Heinrichsthal (DE); Dieter Teusch, Bruchköbel (DE)

(73) Assignee: HERAEUS NEXENSOS GMBH, Kleinostheim (DE)

( * ) Notice: Subject to any disclaimer, the term of this patent is extended or adjusted under 35 U.S.C. 154(b) by 96 days.

(21) Appl. No.: 15/129,288

(22) PCT Filed: Mar. 25, 2015

(86) PCT No.: PCT/EP2015/056356
§ 371 (c)(1),
(2) Date: Sep. 26, 2016

(87) PCT Pub. No.: WO2015/144748
PCT Pub. Date: Oct. 1, 2015

(65) Prior Publication Data
US 2017/0110225 A1   Apr. 20, 2017

(30) Foreign Application Priority Data

Mar. 26, 2014 (DE) .................. 10 2014 104 219

(51) Int. Cl.
*H01C 1/016* (2006.01)
*H01C 7/00* (2006.01)
(Continued)

(52) U.S. Cl.
CPC ............. *H01C 1/016* (2013.01); *G01K 7/183* (2013.01); *H01C 3/12* (2013.01); *H01C 7/006* (2013.01);
(Continued)

(58) Field of Classification Search
CPC .......... H01C 1/016; H01C 3/12; H01C 7/006; H01C 17/065; H01C 17/06526;
(Continued)

(56) References Cited

U.S. PATENT DOCUMENTS 3,928,837 A * 12/1975 Esper ..................... H01C 7/046
338/32 R
4,146,957 A * 4/1979 Toenshoff .............. G01K 7/183
29/612

(Continued)

FOREIGN PATENT DOCUMENTS

DE    36 34 132 A1   4/1987
DE    195 40 194 C1   2/1997
(Continued)

OTHER PUBLICATIONS

English machine translation of JPH0666611 to Nunokawa et al.—Mar. 11, 1994 (Year: 1994).*
(Continued)

*Primary Examiner* — Lisa M Caputo
*Assistant Examiner* — Philip L Cotey
(74) *Attorney, Agent, or Firm* — Hassan Abbas Shakir; Shakir Law PLLC (57) ABSTRACT

An $Al_2O_3$ carrier has a thin-film structure of platinum or a platinum alloy arranged thereon. The carrier and/or the thin-film structure are adapted to reduce mechanical stresses owing to different thermal expansion coefficients. The carrier and/or the thin-film structure include a surface of the carrier in the region of the thin-film structure is smoothed at (Continued)

least in sections to reduce the adhesion and/or a surface of the carrier has an intermediate layer on which the thin-film structure is arranged. The thermal expansion coefficient of the intermediate layer is from $8*10^{-6}$/K to $16*10^{-6}$/K, in particular from $8.5*10^{-6}$/K to $14*10^{-6}$/K, and/or the thin-film structure has at least one conductor path that is undular at least in sections, said conductor path extends laterally along the surface of the carrier.

19 Claims, 5 Drawing Sheets

(51) Int. Cl.
| | | |
|---|---|---|
| *G01K 7/18* | (2006.01) | |
| *H01C 3/12* | (2006.01) | |
| *H01C 17/08* | (2006.01) | |
| *H01C 17/065* | (2006.01) | |
| *H05B 3/12* | (2006.01) | |
| *H01C 17/075* | (2006.01) | |
| *G01N 15/00* | (2006.01) | |
| *G01N 15/06* | (2006.01) | |

(52) U.S. Cl.
CPC ..... *H01C 17/065* (2013.01); *H01C 17/06526* (2013.01); *H01C 17/075* (2013.01); *H01C 17/08* (2013.01); *H05B 3/12* (2013.01); *G01N 15/0606* (2013.01); *G01N 15/0656* (2013.01); *G01N 2015/0046* (2013.01)

(58) Field of Classification Search
CPC ...... H01C 17/075; H01C 17/08; G01K 7/183; H05B 3/12; G01N 15/0606; G01N 15/0656; G01N 2015/0046
See application file for complete search history.

(56) References Cited

U.S. PATENT DOCUMENTS

| | | | |
|---|---|---|---|
| 4,705,713 | A | 11/1987 | Ohta et al. |
| 4,719,441 | A | 1/1988 | Horn |
| 5,140,393 | A | 8/1992 | Hijikihigawa |
| 5,202,665 | A | 4/1993 | Hafele |
| 5,659,127 | A | 8/1997 | Shie et al. |
| 5,831,512 | A | 11/1998 | Wienand et al. |
| 6,450,025 | B1* | 9/2002 | Wado .............. B81B 3/0072 73/204.26 |
| 2002/0142478 | A1* | 10/2002 | Wado .............. G01N 27/124 436/151 |
| 2002/0175076 | A1* | 11/2002 | Gora .............. B82Y 30/00 204/421 |
| 2003/0006139 | A1* | 1/2003 | Noda .............. G01N 27/4073 204/424 |
| 2003/0205698 | A1* | 11/2003 | Ogata .............. C04B 35/016 252/500 |
| 2006/0002815 | A1 | 1/2006 | Harris et al. |
| 2006/0087399 | A1* | 4/2006 | Barge .............. H01C 17/003 338/307 |
| 2006/0237438 | A1* | 10/2006 | Wilkins .............. G01K 7/18 219/505 |
| 2008/0011052 | A1 | 1/2008 | Kondo |
| 2009/0000396 | A1 | 1/2009 | Kawanishi |
| 2009/0115567 | A1* | 5/2009 | Wienand .............. G01K 1/10 338/25 |
| 2010/0117784 | A1 | 5/2010 | Holoubek |
| 2010/0301344 | A1* | 12/2010 | Wu .............. H01L 21/02123 257/66 |
| 2012/0073970 | A1* | 3/2012 | Wang .............. G01N 27/333 204/416 |
| 2012/0324981 | A1* | 12/2012 | Hedayat .............. G01N 15/0656 73/23.33 |
| 2014/0071216 | A1* | 3/2014 | Hu .............. B41J 11/0015 347/102 |
| 2015/0292955 | A1* | 10/2015 | Wienand .............. G01K 1/08 374/185 |
| 2015/0316422 | A1* | 11/2015 | Oya .............. G01K 13/02 374/185 |

FOREIGN PATENT DOCUMENTS

| | | |
|---|---|---|
| DE | 197 42 696 A1 | 5/1999 |
| DE | 199 18 003 A1 | 1/2000 |
| DE | 10331838 B3 | 9/2004 |
| DE | 102006012088 A1 | 9/2007 |
| EP | 0193015 A2 | 9/1986 |
| EP | 2801803 A1 | 11/2014 |
| GB | 2183344 A | 6/1987 |
| JP | S51-068280 A | 6/1976 |
| JP | S55-106740 A | 8/1980 |
| JP | S57-029848 | 2/1982 |
| JP | 59065216 A | 4/1984 |
| JP | S60209127 A | 10/1985 |
| JP | S61-188901 | 8/1986 |
| JP | S62-083641 A | 4/1987 |
| JP | S62-284216 A | 12/1987 |
| JP | H01-185416 A | 7/1989 |
| JP | H03-103721 A | 4/1991 |
| JP | H4-279831 A | 10/1992 |
| JP | H06-066611 A | 3/1994 |
| JP | H09-145489 A | 6/1997 |
| JP | H09145489 A | 6/1997 |
| JP | 2001-050822 A | 2/2001 |
| JP | 2004363264 A | 12/2004 |
| JP | 2007-294870 A | 11/2007 |
| JP | 2007294870 A | 11/2007 |
| JP | 2009085952 | 4/2009 |
| JP | 2014006052 | 1/2014 |
| KR | 20090033131 A | 4/2009 |
| TW | 314593 | 9/1997 |

OTHER PUBLICATIONS

International Search Report dated Jun. 25, 2015 for PCT/EP2015/056356, translation provided.
Written Opinion dated Oct. 1, 2015 for PCT/EP2015/056356.
Official Action dated Oct. 17, 2016 by Taiwanese Intellectual Property Office in related application TW 104109549, machine translation of text provided.
International Preliminary Report on Patentability dated Oct. 6, 2016 for PCT/EP2015/056356 and Written Opinion of of the International Searching Authority for PCT/EP2015/056356, translation provided.
Office Action dated Feb. 8, 2015 issued by the German Patent Office (DPMA) in related application DE 10 2014 104 219.0, partial machine translation provided.
Qu W et al: "A thin-film sensing element for ozone, humidity and temperature", Sensors and Actuators B: Chemical: International Journal Devoted to Research and Development of Physical and Chemical Transducers, Elsevier S.A, CH, vol. 64, No. 1-3, Jun. 1, 2000 (Jun. 1, 2000), pp. 42-48, XP004199283, ISSN: 0925-4005, DOI: 10.101 6/S0925-4005(99) 00481-5, cited in Written Opinion of of the International Searching Authority for PCT/EP2015/056356.
Office Action dated Jan. 23, 2019 by the Japanese Patent Office in related Japanese patent application JP 2016-559256, translation provided.
Wenmin Qu and Wojtek Wlodarski, Article "A thin-film sensing element for ozone, humidity and temperature" in publication Sensors and Actuators B:Chemical, publisher Elsevier, copyright 2000, section 64/1-3, pp. 422-448, cited in Office Action dated Jan. 23, 2019 by the Japanese Patent Office in related Japanese patent application JP 2016-559256.
Office Action dated Jul. 11, 2018 issued by the German Patent Office in related patent application DE 10 2014 104 219.0, partial machine translation provided.

(56) References Cited

OTHER PUBLICATIONS

W. Martienssen, H. Warlimont (Hrsg.), Springer Handbook of Condensed Matter and Materials Data, Publsisher Springer-Verlag, Berlin, 2005; Chapter 3.2, pp. 438 and 440, cited in Office Action dated Jul. 11, 2018 issued by the German Patent Office in related patent application DE 10 2014 104 219.0.
Office Action dated Jul. 24, 2018 by the Japanese Patent Office in related Japanese Patent Application 2016-559256, translation provided.
Office Action dated Jul. 31, 2018 by the Korean Intellectual Property Office in related Korean Patent Application 10-2016-7026193, partial machine translation provided.
Office Action dated Jun. 25, 2019 by the Japanese Patent Office in related Japanese Patent Application 2016-559256, translation provided.

* cited by examiner

CERAMIC CARRIER AND SENSOR ELEMENT, HEATING ELEMENT AND SENSOR MODULE, EACH WITH A CERAMIC CARRIER AND METHOD FOR MANUFACTURING A CERAMIC CARRIER

BACKGROUND OF THE INVENTION

1. Field of the Invention

The invention relates to a ceramic carrier, in particular to an $Al_2O_3$ carrier.

2. Discussion of the Related Art

A carrier of this type is known, for example, from JP 59 065 216 A. Said carrier is coated with a thin-film structure made of platinum and is used as a flow sensor for flow measurement.

Sensors with the same design principle are used as temperature measurement sensors in exhaust gas sensor systems. These are installed upstream of diesel soot particle filters, for example, in order to sense the exhaust gas temperature for regeneration of the filters. In this respect, the platinum thin-film sensors are exposed to severe fluctuating thermal loads, which have to be taken into consideration when designing the sensors with a view to the service life required in the automotive industry. The same applies to the use of platinum thin-film sensors in the automotive industry for monitoring the state of engine oil, the tribological properties of which depend greatly on the heating. For determining the state of the engine oil, the sum of the thermal loads is a crucial measured variable ascertained by platinum temperature sensors. In this respect, the sensors are exposed to many temperature change cycles, severe vibrational loading and to corrosive attack by the measurement medium.

Since the electrical resistance of a platinum sensor changes in an exactly defined manner with the temperature, the avoidance of measurement errors depends on suppressing as far as possible other influencing variables which alter the electrical resistance. In the case of severe fluctuating thermal loads, this problem arises when different materials are paired, as is the case for a ceramic carrier with a platinum thin-film structure. The different materials have different coefficients of thermal expansion, this also being referred to as a mismatch. In the case of fluctuating thermal loads, the different thermal properties of the materials lead to the plastic deformation of the platinum structures and to the migration of dislocations in the microstructure. The material properties are changed as a result. This leads to resistance drifts, i.e. undesired, mechanically induced changes in the resistance. Given severe mechanical stresses in the platinum structures, the latter can even be damaged or interrupted.

To date, attempts have been made to counter this problem by using material pairings which have similar coefficients of thermal expansion. By way of example, ceramic carriers made of zirconium oxide are used in combination with platinum thin-film structures. However, these have the disadvantage that the components structured in this way, in the event of further mechanical installation on $Al_2O_3$ ceramic hybrid carriers or modules, crack and are destroyed at the latest during cooling as a result of the higher level of expansion.

Another route is pursued in the prior art cited in the introduction. There, an attempt is made to reduce thermally induced stresses using a glass layer between the carrier and the platinum thin film. A sensor with such a structure does not satisfy the high demands made in respect of the stability and durability of thin-film sensors in the automotive industry.

SUMMARY OF THE INVENTION

The invention is based on the object of specifying a ceramic carrier on which there is arranged a thin-film structure made of platinum or a platinum alloy, the carrier being improved to the effect that the resistance drift is reduced in the case of high fluctuating thermal loads. The invention is based on the further object of specifying a sensor element, a heating element and a sensor module comprising such a carrier and also a method for producing such a ceramic carrier.

The invention involves the specification of a ceramic carrier, in particular an $Al_2O_3$ carrier, on which there is arranged a thin-film structure made of platinum or a platinum alloy. The carrier and/or the thin-film structure are adapted for reducing mechanical stresses owing to different coefficients of thermal expansion. This is achieved, according to the invention, by the following features of the carrier, which seen individually each reduce the resistance drift. A combination of the features reinforces this effect.

The features specified hereinbelow each realize the basic concept of reducing or relieving mechanical stresses in the thin-film structure owing to the different coefficients of thermal expansion between the carrier and the thin-film structure. To this end, a relative movement between the carrier and the thin-film structure at least in portions is permitted and/or the thin-film structure is modified in such a way that differences in the thermally induced material expansion are compensated for, and therefore the lowest possible mechanical stresses are induced in the thin-film structure.

Specifically, in the context of the invention this is achieved in that the surface of the carrier in the region of the thin-film structure is smoothed at least in portions for reducing the adhesion (feature a).

By virtue of the reduction in the roughness, the thin-film structure adheres to a lesser degree on the carrier surface, as a result of which a relative movement between the carrier and the thin-film structure is made possible. The mechanical decoupling thereby achieved reduces the risk of plastic deformation of the thin-film structure owing to the different expansion between the carrier and the thin-film structure.

In addition or as an alternative, the surface of the carrier has an intermediate layer, on which the thin-film structure is arranged. The coefficient of thermal expansion of the intermediate layer is from $8*10^{-6}/K$ to $16*10^{-6}/K$, in particular from $8.5*10^{-6}/K$ to $14*10^{-6}/K$ (feature b).

It has been found that, by setting the coefficient of thermal expansion of the intermediate layer in the aforementioned range, it is possible to achieve an optimum connection between the ceramic carrier and the platinum thin-film structure which does not lead to significant deformation of the platinum thin-film structure, even in the case of frequent temperature change cycles. The intermediate layer thus provides an effective transition from the carrier to the platinum thin-film structure which acts as a buffer and absorbs some of the mechanical stresses.

In addition or as an alternative, the thin-film structure has at least one conductor track, which is undular at least in portions and which extends laterally along the surface of the carrier (feature c). The undulation of the conductor track extends in a plane which runs parallel to the surface of the carrier. The undulation is thus formed laterally and not in the direction of depth, i.e. into the surface of the carrier. The undulation can extend in one and the same plane parallel to the surface of the carrier. This is the case if the surface of the carrier is without a profile, i.e. is continuously straight. It is also possible for the lateral undulation to be superposed with a further undulation in the direction of depth of the carrier. This arises, for example, through the combination with the depth profile described further below. The main orientation of the undulation runs in the lateral direction.

The amplitude of the undular conductor track is from 0.2*B to 2*B, in particular from 0.4*B to 1*B. The wavelength of the undular conductor track is from 3*B to 10*B, in particular from 4*B to 7*B. Here, "B" is in each case the width of the conductor track.

By virtue of its geometry, the undular conductor track relieves mechanical stresses which are produced in the thin-film structure on account of the different expansion of the carrier and of the thin-film structure. As a whole, what results is reduced deformation of the undular conductor track in contrast to a straight, i.e. non-undular, conductor track. The stress concentration in the conductor track can be influenced in a targeted manner by the geometry of the undulation.

In addition or as an alternative, a first cover layer containing oxidic nanoparticles, in particular of $Al_2O_3$ and/or MgO, is applied to the thin-film structure (feature d).

The first cover layer forms a passivation layer and protects the platinum thin-film structure. The oxidic nanoparticles change the volume of the cover layer in the case of a change in temperature which is adapted to the expansion of the platinum thin-film structure.

It has been found that the following combinations of features a, b, c and d effectively reduce the resistance drifting. Other combinations of features are not excluded.

Feature d with in each case one of features a, b, c;
Features a and c and d;
Features b and c and d;
Features a and b and c and d.

In a preferred embodiment of the invention, the surface in the region of the thin-film structure forms at least one sliding portion and at least one adhesive portion.

The roughness of the surface of the carrier is higher in the region of the adhesive portion than in the region of the sliding portion. In other words, the sliding portion is smoothed. The adhesive portion is unsmoothed or smoothed to a lesser extent than the sliding portion.

This has the advantage that the good adhesion of the untreated surface is retained in uncritical regions of the thin-film structure (adhesive portion) and the adhesion is reduced in a targeted manner in regions in which large stresses are established in the event of temperature changes (sliding portion). In an extreme case, there is a relative movement between the surface of the carrier and the thin-film structure in the region of the sliding portion. In the region of the adhesive portion or of the adhesive portions, the thin-film structure remains connected to the surface of the carrier. The thin-film structure is thereby fixed to the carrier in certain portions and decoupled from the carrier in certain portions, inasmuch as relative movements between the surface of the carrier and the thin-film structure are permitted.

Alternatively, the surface in the entire region of the thin-film structure can be smoothed. This variant has the advantage of simple production. The fixing of the thin-film structure is adequate, since, on account of the inhomogeneous temperature distribution which typically arises during operation, local thermally induced stresses are generated and portions of the thin-film structure are subjected to different levels of loading.

It is preferable that the surface in the region of the thin-film structure has an, in particular strip-shaped, depth profile which forms at least one recess, wherein the surface of the recess is smoothed. The surface of the recess has a lower roughness than the surface of those regions of the depth profile which are located higher, for example the unprofiled surface regions of the carrier.

This has the effect that the thin-film structure can break away from the recess in the event of expansion. In this way, the thin-film structure is partially mechanically decoupled from the carrier. Moreover, the thin-film structure can become stretched in the region of the recess upon detachment and thereby changes its geometry, such that mechanical stresses in the thin-film structure are reduced as a result.

In a preferred embodiment, at least one conductor track of the thin-film structure is arranged at an angle, in particular in the range of 30° to 90°, in relation to the strip-shaped depth profile. This embodiment brings about an effective compensation of expansion in conjunction with a typical conductor track structure. In the case of meandering conductor tracks, these repeatedly cross the strip-shaped depth profile, such that the compensation of expansion takes effect at a plurality of points of the conductor track. This also applies to carriers comprising a plurality of individual conductor tracks.

The recess can have a trapezoidal cross section with two inclined flanks and a base between the flanks. The two flanks laterally delimit the base of the recess. At least one flank, in particular both flanks, rise at an angle of 10° to 80°, in particular of 45° to 60°, with respect to the base. The angle is measured between an imaginary plane spanning the base and a further imaginary plane defining the flank in question. This embodiment has the advantage that the thin-film structure can readily break away from the recess. This is due to the inclined walls or flanks of the recess.

It is preferable that the flanks and the base of the recess are smoothed. This facilitates the detachment further.

It is preferable that the recess has a depth of 0.4 µm to 1.2 µm, in particular of 0.6 µm to 1.0 µm, and/or a width of 5 µm to 20 µm, in particular of 10 µm to 15 µm. The dimensions of the recess are chosen, inter alia, depending on the respective layer thickness of the structure.

The strip-shaped depth profile can have a plurality of parallel recesses, wherein the spacing between the recesses is in each case from 5 µm to 20 µm, in particular from 10 µm to 15 µm. The individual conductor track or plurality of conductor tracks intersect the parallel recesses, such that the compensation of expansion is effected repeatedly along the length of the conductor track or conductor tracks. This achieves the advantage of reducing the resistance drift along the entire conductor track and/or in particularly critical conductor track portions.

In a preferred embodiment, the coefficient of thermal expansion of the intermediate layer is greater at most by the factor of 1.5 than the coefficient of thermal expansion of the thin-film structure. It has proved to be expedient to limit the upper limit of the coefficient of thermal expansion of the intermediate layer, in order to optimize the buffering action of the intermediate layer.

The thickness of the intermediate layer can be from 0.2 µm to 3 µm, in particular from 1 µm to 2.2 µm. These thickness ranges have proved to be expedient in practice.

The intermediate layer can contain at least one electrically insulating metal oxide. In particular, the intermediate layer can consist entirely of an electrically insulating metal oxide. Since the metal oxide is electrically insulated, continuous regions of the carrier can be coated with the metal oxide as the intermediate layer, without the function of the platinum thin-film structure thereby being impaired.

In a particularly preferred embodiment, the intermediate layer contains MgO and/or BaO. The intermediate layer can consist entirely of MgO and/or BaO and unavoidable impurities. As an alternative, the intermediate layer can contain a mixture of at least one electrically insulating metal oxide and $Al_2O_3$ or consist entirely of such a mixture. The metal oxide of the mixture can be MgO and/or BaO. The mixture with $Al_2O_3$ has the advantage that the coefficient of thermal expansion of the intermediate layer can be varied by setting the $Al_2O_3$ content and can thus be adapted optimally to the respective material pairing of the carrier and the platinum thin-film structure and also to the thermal and mechanical requirements.

In a further, particularly preferred embodiment, the undular conductor track has a plurality of arcs extending laterally along the surface, wherein an undular substructure is formed at least in the conductor track portions between the arcs. As an alternative, the undular conductor track can form a plurality of fingers of an electrode which are arranged in a comb-like manner.

In the case of a typical sensor element, for example for temperature measurement, the conductor track arrangement has a meandering structure. The meandering shape of the conductor track forms a superstructure. The undulation of the conductor track forms a substructure, which is integrated into the superstructure and extends along the conductor track portions between the arcs of the superstructure. The formation of the substructure and the effect thereof on the resistance drift are substantially independent of the formation of the superstructure. In this respect, the term "arcs" is to be understood broadly, and can encompass rounded or rectangular changes in direction in the conductor tracks.

The undular conductor track can be embodied in the form of a sine wave and/or a sawtooth-shaped wave and/or a trapezoidal wave. The different geometry of the waves has an effect on the stress concentration distribution in the conductor track in the event of fluctuating thermal loads. The geometry is chosen taking into account the respective conditions of use of the carrier.

The first cover layer can be sealed hermetically by a second cover layer, in particular made of glass. As a result, the first cover layer, or the entire platinum thin-film structure, is reliably protected against the corrosive attack of the measurement medium.

The carrier is integrated in a sensor element or heating element or in a sensor module. Possible sensor elements are, for example, temperature sensor elements, flow sensors, soot sensors and the like. The carrier according to the invention can be a component part of a heating element. Sensor modules are basic modules which have a multi-functional structure and are based on platinum thin-film technology. They consist, for example, of sensor/heater combinations and electrodes structured in a manner specific to the application. Sensitive layers can be applied to the electrodes by the customer.

In a preferred embodiment of the sensor module, various sensor structures are arranged on the carrier. In this respect, the thin-film structure made of platinum or the platinum alloy can form at least one sensor structure and an electrode structure can form at least one further sensor structure. Specifically, the platinum thin-film structure can form a temperature sensor/heater combination.

The method for producing a ceramic carrier involves removing, and thereby smoothing, the surface of the carrier at least in the region of the thin-film structure by etching, in particular plasma ion etching. In addition or as an alternative, the intermediate layer can be applied to the surface of the carrier by a thin-film method, in particular a PVD or CVD method. In addition or as an alternative, the undular conductor track can be applied to the surface of the carrier by a thin-film method, in particular a PVD or CVD method or a lithography method.

BRIEF DESCRIPTION OF THE FIGURES

The invention will be explained with further details hereinbelow on the basis of exemplary embodiments and with reference to the appended drawings.

In said drawings, schematically.

DETAILED DESCRIPTION OF THE INVENTION

Figure 1:
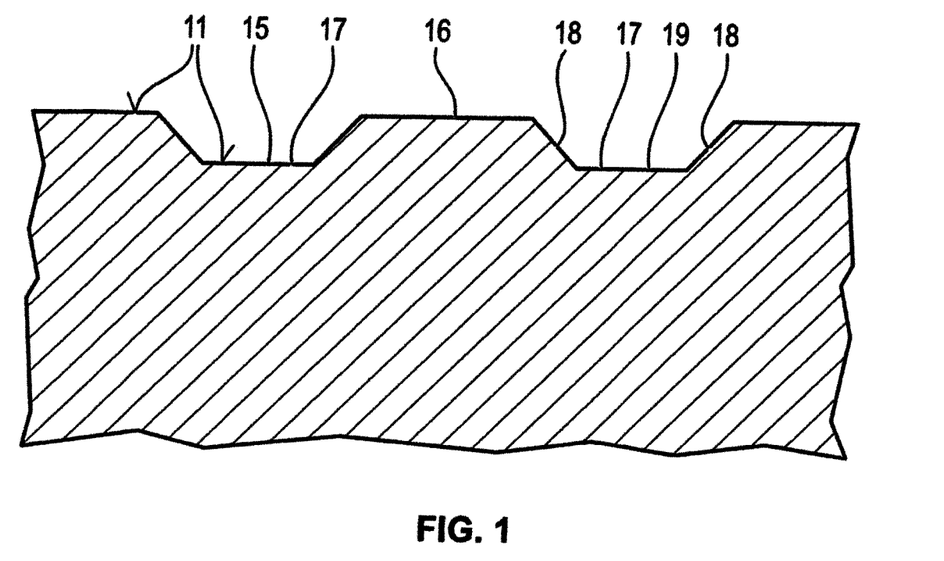
FIG. 1 shows a section through a carrier according to one exemplary embodiment according to the invention, in which the surface is structured by a depth profile.

FIG. 1 shows a section through a ceramic carrier according to one exemplary embodiment according to the invention. Specifically, the ceramic carrier is an $Al_2O_3$ carrier (aluminum oxide carrier). The carrier serves as a substrate, or as a ceramic support, for a thin-film structure (not shown in FIG. 1). $Al_2O_3$ has proved to be expedient as the material for the ceramic carrier, in particular with at least 96% by weight and preferably more than 99% by weight $Al_2O_3$. The carrier can be in the form of a plate with a thickness in the range of 100 μm to 1000 μm, in particular 150 μm to 650 μm. Other plate thicknesses are possible. With a view to the thermal response behavior, the thickness of the carrier should be chosen to be as thin as possible. Particularly in applications in the automotive sector, in which severe vibrational loading often occurs, the mechanical stability of the carrier determines the lower limit of the plate thickness. The ceramic carrier can be in the form of a rectangular plate. Other shapes of the carrier are possible.

The above statements in relation to the general shape of the carrier and in relation to the material composition apply in general terms to the invention and are disclosed in conjunction with all exemplary embodiments.

The carrier as shown in FIG. 1 is adapted for reducing the mechanical stresses owing to different coefficients of thermal expansion of the materials used. To this end, the surface of the carrier in the region of the thin-film structure is smoothed. There are two possibilities for this purpose. Either the carrier is smoothed in the entire region of the thin-film structure, which is easy to realize in terms of production, or the carrier is smoothed partially in the region of the thin-film structure.

The smoothed surface 11 has the effect that the adhesion of the thin-film structure is reduced, and therefore the latter can slide on the surface 11 of the carrier in order to compensate for differences in linear expansion. If the surface 11 is smoothed only partially in the critical regions, the untreated surface regions ensure the adhesion for the thin-film structure. One example of this is shown in FIG. 1, in which the surface 11 has a strip-shaped depth profile which forms at least one recess 17, wherein the surface of the recess 17 is smoothed. The regions of the surface 11 which directly adjoin the recess 17 on both sides are untreated. As a result, the surface 11 of the carrier forms a sliding portion 15 in the region of the recess 17, said sliding portion being laterally delimited in each case by an adhesive portion 16. The adhesive portion 16 is formed by the surface regions which adjoin the recess 17.

Figure 2:
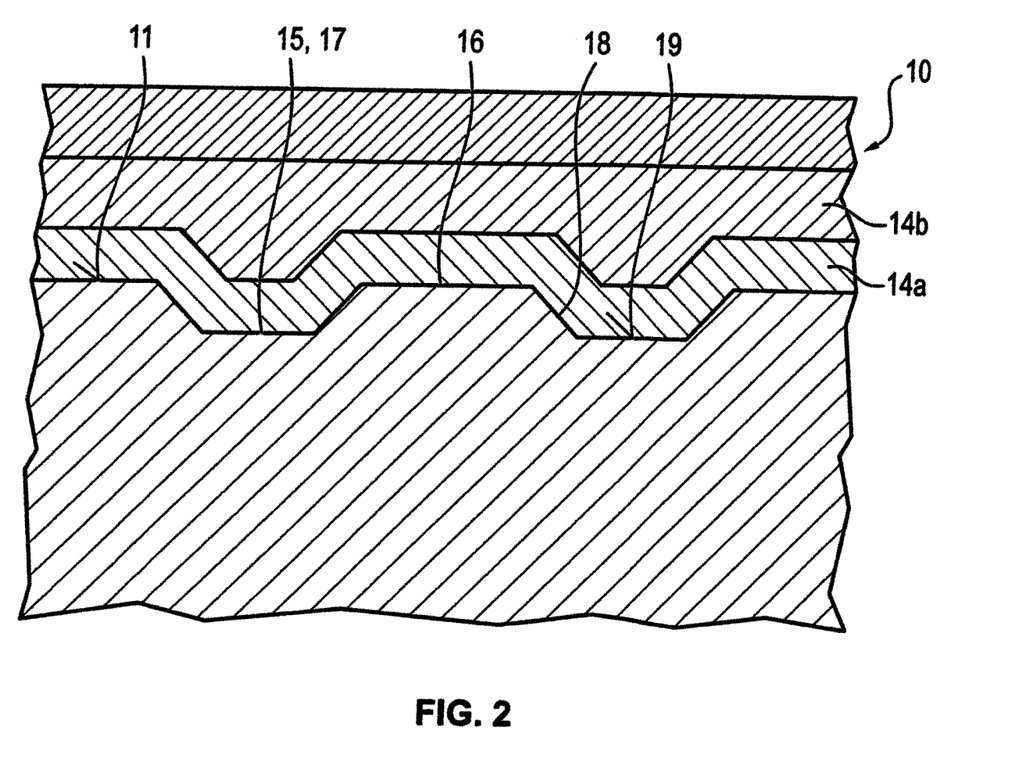
FIG. 2 shows a section through a carrier according to a further exemplary embodiment according to the invention, the surface of which is structured in the same way as in FIG. 1 and is additionally coated with the platinum thin-film structure.

In the region of the sliding portion 15, or of the recess 17, the adhesion between the platinum thin-film structure shown in FIG. 2 and the carrier is reduced. In the event of linear expansion of the platinum thin-film structure 10, this can lead to detachment of the latter in the region of the recess 17. Those surface regions of the carrier which adjoin the recess 17 are untreated, and therefore the roughness is higher in these regions than in the region of the recess 17. The adhesive portions 16 thus formed fix the platinum thin-film structure 10 between the sliding portions 15, or the recesses 17. In the event of linear expansion of the platinum thin-film structure, the latter breaks away in the region of the recess 17 and can be stretched. This change in the geometry of the platinum thin-film structure 10, together with the detachment from the carrier, has the effect that deformation of the platinum thin-film structure 10 owing to the different coefficients of thermal expansion of the carrier and of the structure 10 is largely avoided.

The detachment of the platinum thin-film structure 10 from the surface 11 is facilitated by the fact that the recess 17 has a trapezoidal cross section. The cross section is determined by two flanks 18, which are arranged in an inclined manner and laterally delimit a base 19 of the recess 17. The flanks 18 rise at an angle of 10° to 80°, in particular of 45° to 60°. The angle is determined by a first imaginary plane running through the base 19 and a second imaginary plane running through the flank in question. The depth of the recess 17 can lie in the range of 0.4 μm to 1.2 μm, in particular in the range of 0.6 μm to 1.0 μm. The width can be 5 μm to 20 μm, in particular 10 μm to 15 μm.

As can furthermore be seen in FIG. 1, the strip-shaped depth profile has a plurality of parallel recesses 17 extending along the surface 11 of the carrier. The spacing between the recesses 17 can be from 5 μm to 20 μm, in particular from 10 μm to 15 μm. The recesses 17 are spaced apart equidistantly and in a parallel manner.

Instead of the partially smoothed surface resulting from the formation of the depth profile, the surface can be smoothed without a profile. This means that the surface is smoothed uniformly, without the formation of a depth profile.

The smoothing can be effected by removal of the surface. The removal can be effected by ion etching, in particular plasma ion etching, with a removal depth of 0.2 μm to 2 μm. The partial removal, or the partial smoothing, can be achieved by a resist mask, which is applied prior to the ion etching and protects the covered regions during the etching operation.

Figure 3:
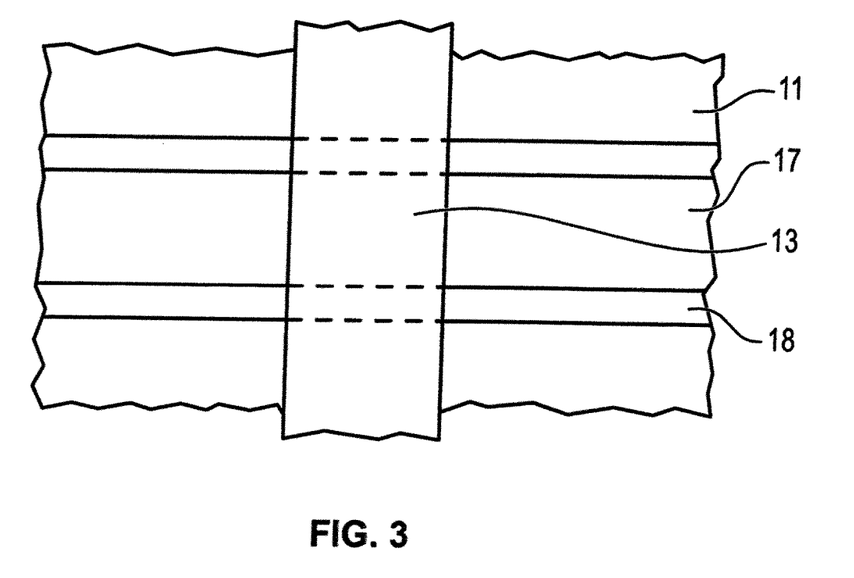
FIG. 3 shows a plan view onto the carrier shown in FIG. 1.

FIGS. 2 and 3 show how the platinum thin-film structure 10 adapts to the depth profile of the carrier. In this respect, FIG. 2 specifically shows that the shape of the depth profile is reflected in the shape of the platinum thin-film structure 10. The method gives rise to a trapezoidal formation of the depth profiles, and this avoids steps (continuous profiling). The platinum thin-film structures 10 follow the depth profile over the entire substrate with an approximately constant layer thickness.

It can be seen in the plan view as shown in FIG. 3 that the conductor track 13 intersects the recess 17 in a transverse manner, i.e. at an angle of 90°. Other angles of intersection are possible, for example depending on the meandering shape of the conductor track 13. The conductor track 13 can intersect the recess 17 at an angle in the range of 30° to 90°.

FIG. 2 moreover illustrates the layer structure above the platinum thin-film structure. A first cover layer 14a is applied directly to the platinum thin-film structure and serves for the passivation of the platinum thin-film structure 13. A second cover layer 14b is applied to the first cover layer 14a and seals the first cover layer 14a hermetically.

Figure 4:
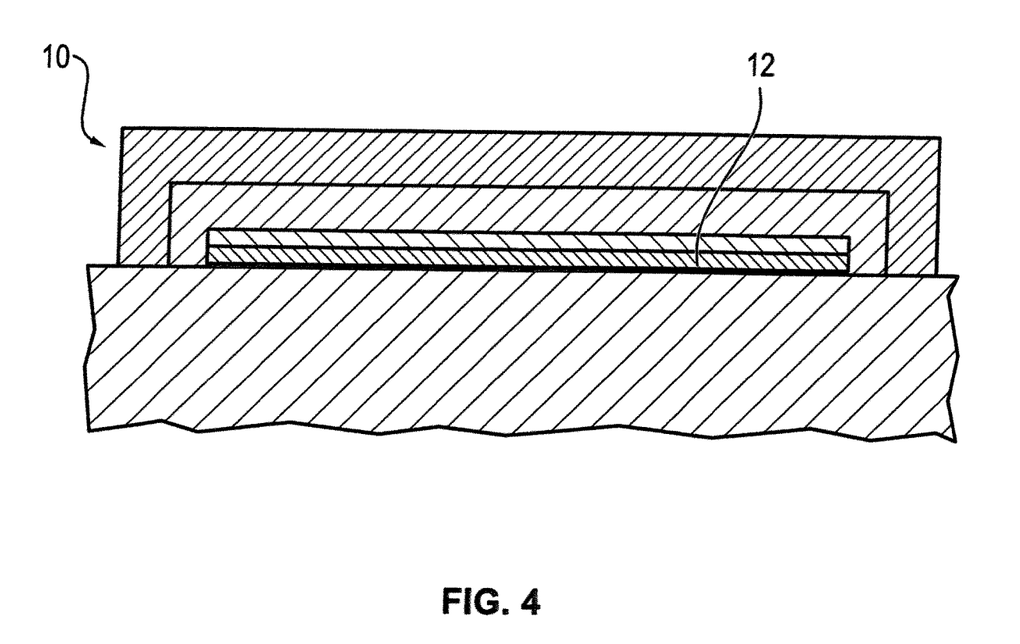
FIG. 4 shows a section through a carrier according to a further exemplary embodiment according to the invention, in which an intermediate layer is arranged between the platinum thin-film structure and the carrier.

FIG. 4 shows a further exemplary embodiment of the invention, in which an intermediate layer 12 is arranged between the carrier and the platinum thin-film structure 10. The intermediate layer 12, which is also referred to as the interface layer, is formed from an electrically insulating metal oxide. This has the function of a buffer, which absorbs the stresses caused by the mismatch and conducts them at least partially into the carrier. The intermediate layer 12 has a greater coefficient of thermal expansion than the ceramic carrier, in particular than $Al_2O_3$, and this may be up to 50% greater than the coefficient of thermal expansion of platinum. A magnesium oxide layer (MgO) applied by thin-film technology and having a layer thickness in the range of 0.2 μm to 3 μm has proved to be expedient in practice. The coefficient of thermal expansion of magnesium oxide is $13*10^{-6}$/K. This coefficient of expansion is greater than the coefficient of expansion of $Al_2O_3$, with $6.5*10^{-6}$/K, and of platinum, with $9.1*10^{-6}$/K. Instead of magnesium oxide (MgO), barium oxide (BaO) can be used for the intermediate layer 12. For setting the coefficient of thermal expansion of the intermediate layer 12, use can be made of a mixture of an electrically insulating metal oxide, for example magnesium oxide, and $Al_2O_3$. The coefficient of thermal expansion of the intermediate layer 12 changes depending on the $Al_2O_3$ content.

A further exemplary embodiment, in which the shape of the conductor track or of the conductor tracks is modified, is shown in FIGS. 5 and 6a-6d. The concept on which this exemplary embodiment is based involves forming the conductor track 13 not in a linear manner, as shown at the top in FIG. 5, but rather in a non-linear manner, in particular in an undular form, as shown at the bottom in FIG. 5. The undulation extending in the lateral direction, i.e. along the surface 11 of the carrier, has the effect that the differences in linear expansion of the platinum thin-film structures are separated into an X and Y component. It has been found that this separation has a positive effect on the stability of the platinum thin-film structures in the event of severe fluctuating thermal loads.

The amplitude of the undular conductor track 13 is from 0.2*B to 2*B, in particular from 0.4*B to 1*B. The wavelength is from 3*B to 10*B, in particular from 4*B to 7*B. Here, "B" denotes the width of the conductor track 13. The terms "amplitude" and "wavelength" are to be understood as meaning the variables which are customary in conjunction with the description of oscillations. The amplitude corresponds to the peak value with respect to the zero line of the undulation. The wavelength corresponds to an oscillation period likewise with respect to the zero line of the wave. The zero line is the axis of symmetry in the longitudinal direction of the wave.

Figure 8:
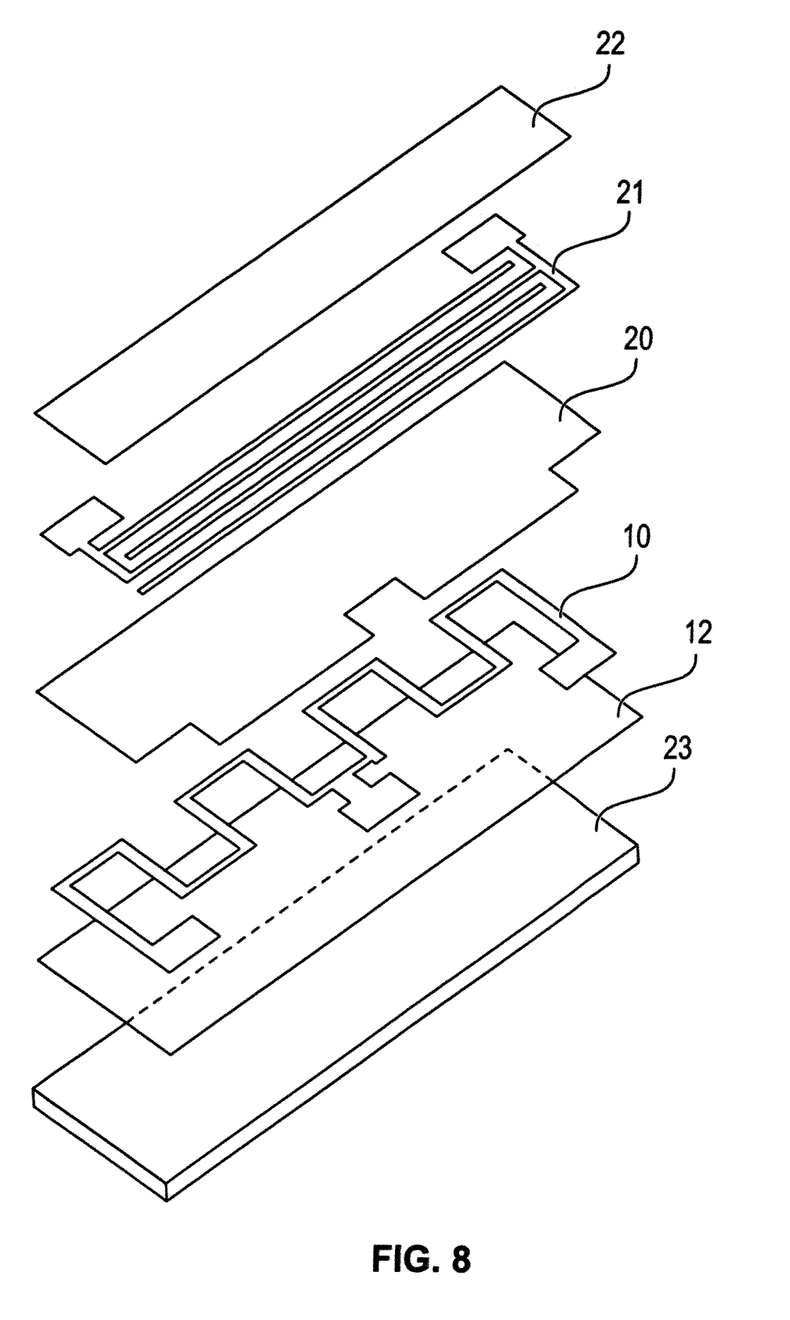
FIG. 8 shows an exploded illustration of a sensor module comprising various thin-film structures which are arranged on a carrier according to one exemplary embodiment according to the invention.

As is shown in FIG. 8, the conductor track 13 can have a superordinate meandering shape, which is to be distinguished from the undulation of the conductor track 13. The meandering shape of the conductor track forms a superstructure, which is superposed by the undulation of the conductor track 13. In this respect, the undulation of the conductor track 13 forms a substructure, which is provided at least in the conductor track portions between the arcs of the meandering shape (superstructure). It is also possible for the arcs of the meandering shape to be provided themselves in the substructure. The term "arc" is also to be understood as meaning a rectangular change in direction in the conductor track, as shown in FIG. 8. The undular conductor track 13 can also form the fingers of the electrode, which are arranged in a comb-like manner (shown in FIG. 8). In this case, the rectilinear finger shape forms the superstructure, which is superposed by the undulation as the substructure.

Figure 5:
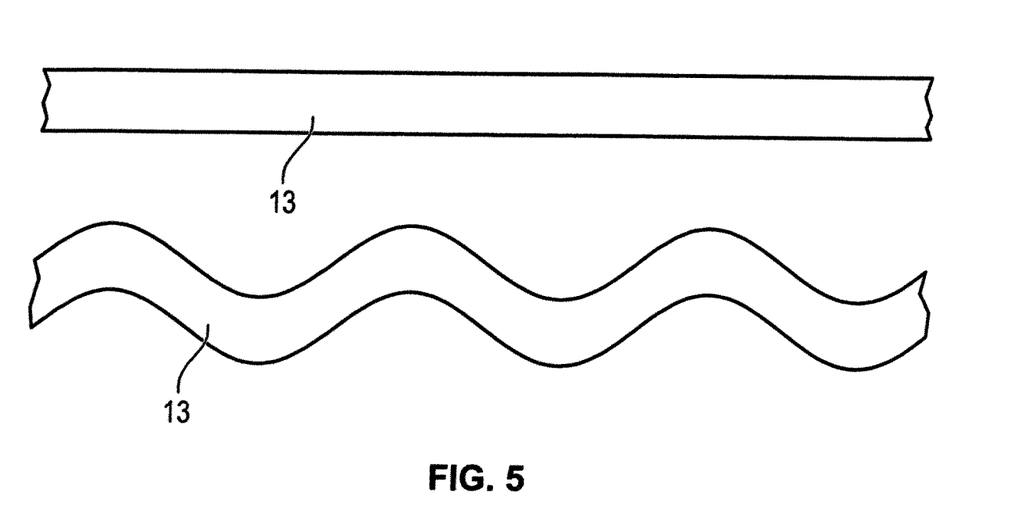
FIG. 5 shows a plan view onto an undular conductor track compared with a rectilinear conductor track.
Figure 6A:
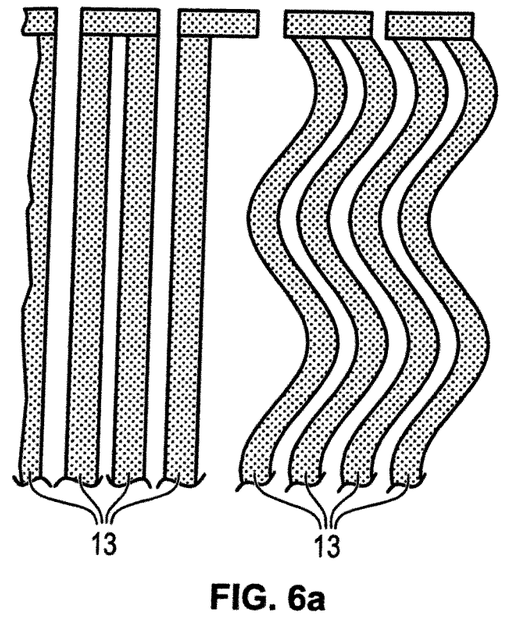
FIGS. 6a-6d show plan views onto undular conductor tracks having different geometries.
Figure 6B:
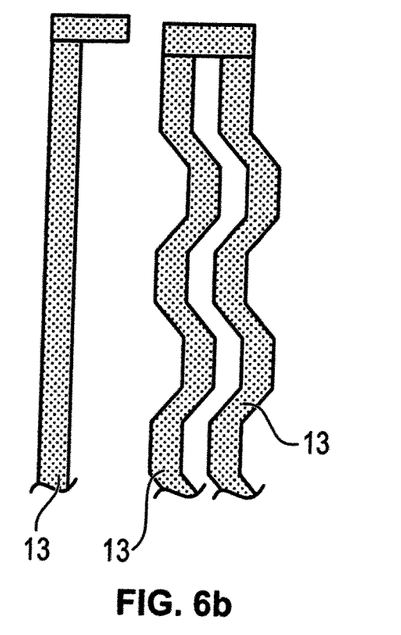
Figure 6C:
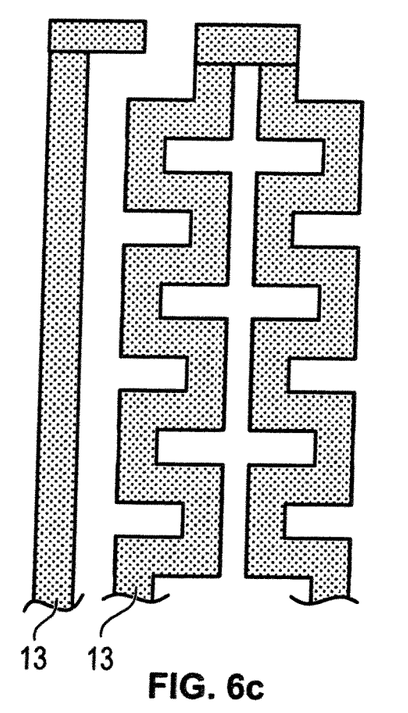
Figure 6D:
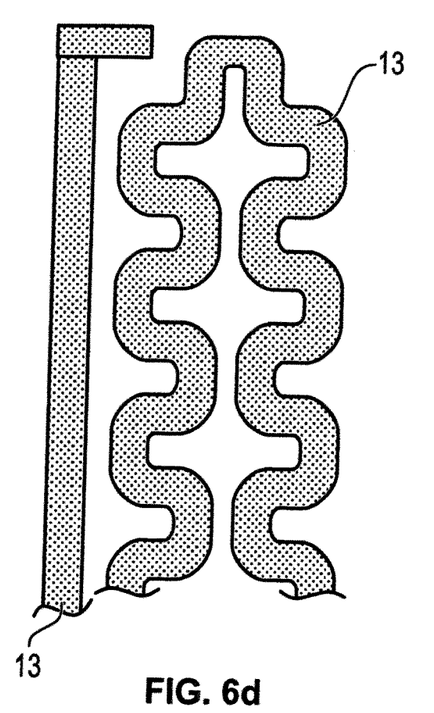

FIGS. 6a to 6d show various geometries of the undulation, these each being contrasted with a rectilinear, wave-free conductor track, similar to in FIG. 5. Thus, FIG. 6a shows that the conductor track 13 can have the shape of a sine wave. A plurality of conductor tracks 13 are arranged alongside one another in phase. FIG. 6b shows an undular conductor track 13, in the case of which the wave has a trapezoidal form. A further example for the wave is shown in FIG. 6c. In this example, the wave has a sawtooth-shaped form. It is also possible to refer to a rectangular meandering shape as the substructure here. The change in direction of the conductor track 13 is effected at an angle of 90°. A mixture of the sine wave shown in FIG. 6a and the sawtooth-shaped wave shown in FIG. 6c is shown in FIG. 6d. In this case, the flanks of the sawtooth-shaped wave are approximated to the sine shape and rounded.

Figure 7:
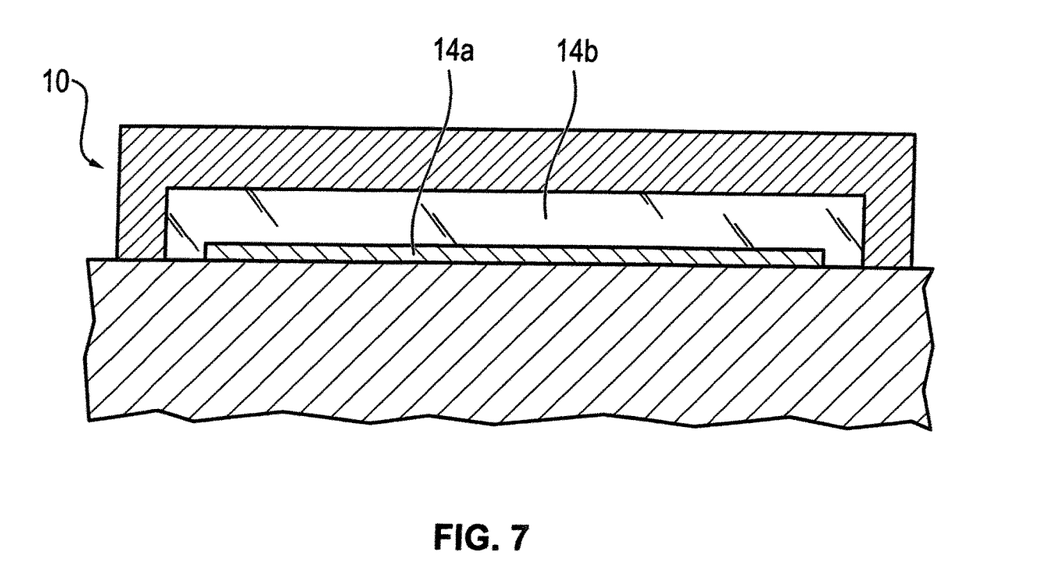
FIG. 7 shows a section through a carrier according to a further exemplary embodiment according to the invention, in which the platinum thin-film structure is protected with a cover layer.

FIG. 7 shows a further exemplary embodiment, in which the first cover layer is modified by the addition of oxidic nanoparticles. This has the effect that the volume of the first cover layer 14a changes upon a change in temperature, this reducing the resistance drift. The first cover layer 14a is sealed hermetically by a second cover layer made of glass.

The exemplary embodiments described above each seen individually improve the dimensional stability of the platinum thin-film structure 10 and thus counteract the resistance drift. The exemplary embodiments are therefore each disclosed independently of one another. In addition, the exemplary embodiments can also be combined with one another, as is shown by way of example with reference to the exemplary embodiment as shown in FIG. 2. The combination of the various exemplary embodiments leads to a synergy effect, which is manifested in an increased reduction in the resistance drift.

Specifically, the first cover layer 14a comprising the oxidic nanoparticles can be combined with all exemplary embodiments, because the generally required passivation of the platinum thin-film structure 10 can thereby be effected in such a way that, in addition to the passivation, the resistance drift is improved. As shown in FIG. 2, the first cover layer 14a is combined with the depth profile and the partially smoothed surface 11. It is also possible, as shown in FIG. 4, to combine the first cover layer 14a with the intermediate layer 12. In addition, the intermediate layer 12 can be used together with the undular conductor track 13. Moreover, it is possible to combine the depth profile as shown in FIG. 2 with the intermediate layer as shown in FIG. 4 and also with the undular conductor track 13 as shown in FIG. 5 or one of the undulations as shown in FIGS. 6a to 6d. The combination of all exemplary embodiments is possible.

The carrier can be used for building up various sensors. By way of example, it is expedient to use the carrier for a temperature sensor having a platinum thin-film structure. The use of a flow measurement sensor is similarly possible, in the case of which a heating element and a temperature measurement element are combined in accordance with the anemometric principle. A further example for the use of the invention is shown in FIG. 8 in conjunction with a sensor module. The sensor module forms a multi-sensor platform and has a carrier substrate 23. The carrier substrate 23 can be modified according to one of the exemplary embodiments explained above. By way of example, a strip-shaped depth profile (not shown) can be formed in the carrier substrate. The intermediate layer 12 is arranged on the carrier substrate 23 and serves as a buffer for the platinum thin-film structure 10 arranged on the intermediate layer 12. The platinum thin-film structure 10 can be a heater and/or sensor in each case with contact connections. An insulation layer 20 is applied to the platinum structure 10, with an interdigital electrode structure 21 for conductivity measurement (IDE) being arranged on said insulation layer. The interdigital electrode structure 21 is provided with an active functional layer 22, which can be applied for example by the customer.

LIST OF REFERENCE SIGNS

10 Thin-film structure
11 Surface
12 Intermediate layer
13 Conductor track
14a First cover layer
14b Second cover layer
15 Sliding portion
16 Adhesive portion
17 Recess
18 Flanks
19 Base
20 Insulation layer
21 Electrode structure
22 Functional layer
23 Carrier substrate

What is claimed is:
1. An $Al_2O_3$ carrier for reducing mechanical stresses, the $Al_2O_3$ carrier comprising:
an $Al_2O_3$ body; and
a thin-film structure comprising platinum or comprising a platinum alloy, the thin-film structure comprising a first coefficient of thermal expansion; and
a surface of the $Al_2O_3$ carrier having an intermediate layer on which the thin-film structure is arranged, the intermediate layer comprising a second coefficient of thermal expansion from $8*10^{-6}$/K to $16*10^{-6}$/K;

wherein $Al_2O_3$ is at least 99% by weight of the $Al_2O_2$ carrier;
wherein the second coefficient of thermal expansion is greater at most by a factor of 1.5 than the first coefficient of thermal expansion; and
wherein the intermediate layer consists of an electrically insulating metal oxide.

2. The $Al_2O_3$ carrier as claimed in claim 1, wherein the surface in a region of the thin-film structure forms at least one sliding portion and at least one adhesive portion.

3. The $Al_2O_3$ carrier as claimed in claim 1, wherein the surface in the region of the thin-film structure has a strip-shaped depth profile which forms at least one recess.

4. The $Al_2O_3$ carrier as claimed in claim 3,
wherein the thin-film structure has at least one conductor track, the at least one conductor track being undular at least in portions and extending laterally along the surface of the $Al_2O_3$ carrier,
wherein the amplitude of the undular conductor track is from 0.2*B to 2*B, and a wavelength of the undular conductor track is from 3*B to 10*B, where "B" is the width of the conductor track,
wherein at least one conductor track of the thin-film structure is arranged at an angle relative to the strip-shaped depth profile.

5. The $Al_2O_3$ carrier as claimed in claim 3,
wherein the at least one recess has a trapezoidal cross section with two inclined flanks and a base between the flanks,
wherein at least one flank rises at an angle of 10° to 80° relative to the base.

6. The $Al_2O_3$ carrier as claimed in claim 3, wherein the at least one recess has a depth of 0.4 μm to 1.2 μm or a width of 5 μm to 20 μm.

7. The $Al_2O_3$ carrier as claimed in claim 3,
wherein the strip-shaped depth profile has a plurality of parallel recesses, and
wherein the spacing between the recesses is in each case from 5 μm to 20 μm.

8. The $Al_2O_3$ carrier as claimed in claim 3, wherein at least one conductor track of the thin-film structure is arranged at an angle of 30° to 90° relative to the strip-shaped depth profile.

9. The $Al_2O_3$ carrier as claimed in claim 1, wherein a thickness of the intermediate layer is from 0.2 μm to 3 μm.

10. The $Al_2O_3$ carrier as claimed in claim 1, wherein the intermediate layer comprises MgO or BaO.

11. The $Al_2O_3$ carrier as claimed in claim 1;
wherein the thin-film structure has at least one conductor track, the at least one conductor track being undular at least in portions and extending laterally along the surface of the $Al_2O_3$ carrier,
wherein the amplitude of the undular conductor track is from 0.2*B to 2*B, and a wavelength of the undular conductor track is from 3*B to 10*B, where "B" is the width of the conductor track,
wherein the undular conductor track comprises a plurality of arcs extending laterally along the surface,
wherein an undular substructure is formed at least in the conductor track portions between the arcs, or the undular conductor track forms a plurality of fingers of an electrode which are arranged in a comb-like manner.

12. The $Al_2O_3$ carrier as claimed of claim 1,
wherein the thin-film structure has at least one conductor track, the at least one conductor track being undular at least in portions and extending laterally along the surface of the $Al_2O_3$ carrier,
wherein the amplitude of the undular conductor track is from 0.2*B to 2*B, and a wavelength of the undular conductor track is from 3*B to 10*B, where "B" is the width of the conductor track,
wherein the undular conductor track is embodied in the form of a sine wave or a sawtooth-shaped wave or a trapezoidal wave.

13. The $Al_2O_3$ carrier as claimed in claim 1, further comprising a first cover layer comprising oxidic nanoparticles of $Al_2O_3$ or MgO and which is applied directly to the thin-film structure.

14. The $Al_2O_3$ carrier as claimed in claim 13, wherein the first cover layer is sealed hermetically by a second cover layer comprising glass.

15. A sensor module, the sensor module comprising:
an $Al_2O_3$ carrier for reducing mechanical stresses, the $Al_2O_3$ carrier comprising
an $Al_2O_3$ body; and
a thin-film structure comprising platinum or comprising a platinum alloy the thin-film structure comprising a first coefficient of thermal expansion; and
a surface of the $Al_2O_3$ carrier having an intermediate layer on which the thin-film structure is arranged, the intermediate layer comprising a second coefficient of thermal expansion from $8*10^{-6}$/K to $16*10^{-6}$/K;
wherein the first cover layer is sealed hermetically by a second cover layer comprising glass;
wherein $Al_2O_3$ is at least 99% by weight of the $Al_2O_3$ carrier;
wherein the second coefficient of thermal expansion is greater at most by a factor of 1.5 than the first coefficient of thermal expansion, and
wherein the intermediate layer consists of an electrically insulating metal oxide.

16. The sensor module as claimed in claim 15, wherein a plurality of sensor structures are arranged on the $Al_2O_3$ carrier, wherein the thin-film structure comprises platinum or a platinum alloy and forms at least one sensor structure and an electrode structure forms at least one further sensor structure.

17. The $Al_2O_3$ carrier as claimed in claim 15, further comprising a first cover layer comprises oxidic nanoparticles of $Al_2O_3$ or MgO and which is applied directly to the thin-film structure.

18. A method of making an $Al_2O_3$ carrier, the $Al_2O_3$ carrier for reducing mechanical stresses, the $Al_2O_3$ carrier comprising
an $Al_2O_3$ body; and
a thin-film structure comprising platinum or comprising a platinum alloy the thin-film structure comprising a first coefficient of thermal expansion; and
a surface of the $Al_2O_3$ carrier having an intermediate layer on which the thin-film structure is arranged, the intermediate layer comprising a second coefficient of thermal expansion from $8*10^{-6}$/K to $16*10^{-6}$/K;
wherein $Al_2O_3$ is at least 99% by weight of the $Al_2O_3$ carrier;
wherein the second coefficient of thermal expansion is greater at most by a factor of 1.5 than the first coefficient of thermal expansion, and
wherein the intermediate layer consists of an electrically insulating metal oxide; the method comprising the steps of:
applying the intermediate layer to the surface of the $Al_2O_3$ carrier by a thin-film method, or
applying the undular conductor track to the surface of the $Al_2O_3$ carrier by the thin-film method.

19. The $Al_2O_3$ carrier as claimed in claim 18, further comprising a first cover layer comprises oxidic nanoparticles of $Al_2O_3$ or MgO and which is applied directly to the thin-film structure.

\* \* \* \* \*